United States Patent [19]
Garlick et al.

[11] Patent Number: 5,362,855
[45] Date of Patent: Nov. 8, 1994

[54] IMIDOESTER CROSS-LINKED HEMOGLOBIN COMPOSITIONS

[75] Inventors: Robert L. Garlick, Augusta; Stephen B. Lyle, Kalamazoo; Joseph P. Martin, Jr., Richland, all of Mich.

[73] Assignee: The Upjohn Company, Kalamazoo, Mich.

[21] Appl. No.: 65,170

[22] Filed: May 20, 1993

Related U.S. Application Data

[63] Continuation of PCT/US91/07155, Oct. 3, 1991, which is a continuation-in-part of Ser. No. 619,840, Nov. 29, 1990, abandoned.

[51] Int. Cl.$^5$ .................... C07C 103/52; A61K 37/00
[52] U.S. Cl. ........................................ 530/385; 514/6
[58] Field of Search ............................ 514/6; 530/385

[56] References Cited

U.S. PATENT DOCUMENTS

| | | | |
|---|---|---|---|
| 3,925,344 | 12/1975 | Mazur | 530/385 |
| 4,001,200 | 1/1977 | Bonsen et al. | 260/112.5 R |
| 4,001,401 | 1/1977 | Bonsen et al. | 424/177 |
| 4,053,590 | 10/1977 | Bonsen et al. | 424/177 |
| 4,061,736 | 12/1977 | Morris et al. | 424/177 |
| 4,777,244 | 10/1988 | Bonhard et al. | 530/385 |
| 4,826,811 | 5/1989 | Sehgal et al. | 514/6 |
| 4,857,636 | 8/1989 | Hsia | 530/385 |

FOREIGN PATENT DOCUMENTS

| | | | |
|---|---|---|---|
| 0195558 | 3/1986 | European Pat. Off. | A61K 37/14 |
| 0181033 | 5/1986 | European Pat. Off. | G01N 33/96 |
| 0361720 | 9/1988 | European Pat. Off. | A61K 37/14 |
| WO88/03408 | 5/1988 | WIPO | A61K 37/04 |

OTHER PUBLICATIONS

Chemical Abstract No. 205961Q, vol. 91, No. 25, Columbus, Ohio, US, R. Pennathur DAS: "Modification of Hemoglobin A with Dimethyl Adipimidate", p. 211 (Dec. 17, 1979).

Chemical Abstract No. 162530, vol. 102, No. 19, Columbus, Ohio, US, R. J. Ferris: "The Crosslinking of Human met-hemoglobin with (c14)dimethyl Adipimidate", p. 252 (May 13, 1985).

Can J. Biochem. Cell. Biol., vol. 63, No. 3, pp. 195–203 (1985).

Feola, M., Gonzalez, H., Canizaro, P. C., Bingham, D. and Periman, P., "Development of a bovine stroma-free hemoglobin solution as a blood substitute," 1983, Surg. Gyn. Obst. 157: 399–408.

Plese, C. F., and Amma, E. L., "Circular dichroism as a probe of the allosteric R–T transformation in hemoglobins and modified hemoglobins," 1977, Biochem. Biophys. Res. Commun. 76; 691–697.

Pennathur-Das, R., Heath, R. H., Mentzer, W. C., and Lubin, B. H., "Modification of hemoglobin S with dimethyl adipimidate. Contribution of individual reacted subunits to changes in properties," 1982, Biochim. Biophys. Acta 704: 389–397.

Pennathur-Das, R., Vickery, L. E., Mentzer, W., and Lubin, B. H., "Modification of hemoglobin A with dimethyl adipimidate. Contribution of individual reacted subunits to changes in oxygen affinity," 1979, Biochim. Biophys. Acta 580: 356–365.

Primary Examiner—Lester L. Lee
Assistant Examiner—P. Lynn Touzeau
Attorney, Agent, or Firm—Donald L. Corneglio

[57] ABSTRACT

An imidoester, cross-linked hemoglobin composition useful in the transport of oxygen to living cells and being essentially free of any impurities, a P50 of at least 13 mm Hg and predominantly in tetramer form. Preferably, the cross-linked hemoglobin composition has a predominant molecular weight of at least 64,000. The purified and cross-linked hemoglobin has improved cross-link stability to autoxidation and can be used as a blood substitute for mammals or as an oxygen transport fluid.

9 Claims, No Drawings

IMIDOESTER CROSS-LINKED HEMOGLOBIN COMPOSITIONS

CROSS-REFERENCE TO RELATED APPLICATIONS

This application is a continuation of International Application PCT/US91/07155, filed Oct. 3, 1991, which is a continuation-in-part of U.S. Ser. No. 07/619,840, filed Nov. 29, 1990, abandoned.

BACKGROUND OF THE INVENTION

The present invention is directed toward a novel process for producing a purified cross-linked hemoglobin product suitable as a blood replacement for transfusion in human beings and in animals or as an oxygen transport fluid. The subject cross-linked hemoglobin product is essentially free of contaminants in that it contains very low levels of bacterial endotoxin and phospholipid.

The structure and function of hemoglobin have been reviewed (Bunn, H. F., and B. G. Forget, *Hemoglobin: Molecular, Genetic and Clinical Aspects*, W. B. Saunders Company, Philadelphia, 690 pp., (1986). Mammalian hemoglobin is a tetramer containing two each of two different types of subunits, alpha and beta. Each subunit is of approximate molecular weight 16,000 and contains a heme group with a central iron atom. The protein portion, or globin functions to keep the heme iron in the reduced or ferrous state, thus to allow the hemoglobin molecule to reversibly bind oxygen.

Mammalian hemoglobin should not be thought of as a static tetramer, that is a single protein species with a molecular weight of 64-68,000. It is instead composed of sub-units connected by noncovalent bonds, and existing in dynamic equilibria involving monomer-dimer and dimer-tetramer interactions. At any moment, the hemoglobin would consist of a certain proportion of monomers with a molecular weight of approximately 16,000, dimers of molecular weight 32,000, and tetramers. The distribution of monomer, dimer, and tetramer species in solution are dependent upon hemoglobin concentration, the ligand state of the hemoglobin, as well as pH and salt composition of the solution in which it is contained.

Mammalian hemoglobin is contained within red blood cells or erythrocytes. In the mammals these specialized cells have lost their nuclei during maturation, and are simply sacs of hemoglobin containing very low concentrations of other proteins. The hemoglobin is contained with circulating erythrocytes for several reasons. First of all, if the hemoglobin were not in cells but instead circulated free in solution, it would readily be cleared from circulation by passage through the capillary walls, the kidney and other sites. Certain invertebrate organisms have solved this problem by evolving polymeric hemoglobins with molecular weights in the millions which are too large to pass through capillaries and the nephron of the kidney. Other functions served by the red cell are to provide a sheltered environment to protect the hemoglobin molecule from proteolytic serum proteins, maintain a balance of ions proper for hemoglobin function, provide an enzyme system which maintains the heme iron in the reduced (functional) state, and control the presence of allosteric effector molecules.

There have been numerous efforts to produce clarified stroma-free hemoglobin solutions for blood replacement transfusion in humans (Pennell, R. B., and W. E. Smith, Preparation of stabilized solutions of hemoglobin. *Blood* 4:380-385, (1949); Rabiner, S. F., Helbert, J. R., Lopas, H., and L. H. Friedman, Evaluation of a strom-free hemoglobin solution for use as a plasma expander. *J. Exp. Med.* 126: 1127-1142 (1967); Christensen, S. M., Medina, F., Winslow, R. W., Snell, S. M., Zegna, A., and M. A. Marini, Preparation of human hemoglobin Ao for possible use as a blood substitute. *J. Biochem. Biophys. Meth.* 17: 143-154 (1988); and Feola, M., Gonzalez, H., Canizaro, P. C., Bingham, D. and P. Periman, Development of a bovine stroma-free hemoglobin solution as a blood substitute. *Surg. Gyn. Obst.* 157: 399-408 (1983)). These solutions contain the hemoglobin in an unmodified state, and the hemoglobin is free to dissociate into its subunits. Infusion of unmodified hemoglobin leads to rapid clearance of the hemoglobin from the circulation. In addition, infusion of unmodified hemoglobin reportedly leads to a host of deleterious effects within the body including nephrotoxicity. The nephrotoxicity associated with unmodified hemoglobin has prompted the Center for Biologics Evaluation and Research of the U.S. Food and Drug Administration to state that unmodified hemoglobin should not be present in a hemoglobin-based oxygen carrier.

There have been numerous reports describing the stabilization of hemoglobin solutions by forming covalent chemical cross-links between the hemoglobin polypeptide chains (Rausch, C. W., and M. Feola, Extra pure semi-synthetic blood substitute, International patent application No. PCT/US87/02967, Int. publication no. WO/88/03408 19 May 1988; Bonhard, K., and N. Kothe Cross-linked hemoglobin of extended shelf life and high oxygen transport capacity and process for preparing same, U.S. Pat. No. 4,777,244; Bucci. E., Razynska, A., Urbaitis, B., and C. Fronticelli Pseudo cross-link of human hemoglobin with mono-(3,5-dibromosalicyl)fumarate. *J. Biol. Chem.* 264:6191-6195 (1989); and U.S. Pat. No. 4,001,200.)

INFORMATION DISCLOSURE STATEMENT

Cross-linked hemoglobin compositions have been described in U.S. Pat. Nos. 4,001,200; 4,011,401; 4,053,590; and 4,061,736. More elaborate forms of cross-linking hemoglobin for subsequent purification have also been disclosed in U.S. Pat. No. 4,857,636.

The preparation and cross-linking of bovine hemoglobin has been described in Feola, M., Gonzalez, H., Canizaro, P. C., Bingham, D. and P. Periman, Development of a bovine stroma-free hemoglobin solution as a blood substitute, *Surg. Gyn. Obst.* 157: 399-408 (1983) and International patent application no. PCT/US87/02967, Int. publication no. WO/88/03408 19 May, 1988.

Dimethyl adipimidate reactions with normal human hemoglobin (HbA) and sickle cell hemoglobin (HbS) have been described in Plese, C. F., and E. L. Amma, Circular dichroism as a probe of the allosteric R-T transformation in hemoglobins and modified hemoglobins (1977). U.S. Pat. No. 3,925,344 (1975) discloses cross-linking hemoglobin with imidoesters to prepare a plasma protein material or plasma expander; however, this material is not suitable as an oxygen transfer fluid. As reported by Pennathur-Das, R., Heath, R. H., Mentzer, W. C., and B. H. Lubin, "Modification of hemoglobin S with dimethyl adipimidate Contribution of individual reacted subunits to changes in properties", Biochim. Biophys. Acta 704: 389–397 (1982), cross-linking with the imidoesters (DMA) increased the oxygen affinity of the hemoglobin which makes it unsuitable for transporting oxygen and releasing it. Pennathur-Das, R., Vickery, L. E., Mentzer, W., and B. H. Lubin, "Modification of hemoglobin A with dimethyl adipimidate. Contribution of individual reacted subunits to changes in oxygen affinity," Biochim. Biophys. Acta 580: 356–365 (1979).

Thus, it is desirable to find a method for cross-linking hemoglobin which makes it stable and predominantly in a tetramer form or tetramer multiples but still has a p50 or oxygen affinity which is low enough to effectively transport oxygen and then release it to the cells of a living organism. Also, it is important that the molecular weight is predominantly at least 64,000 which is the tetramer form of hemoglobin with little to none below 64,000; i.e., dimer or monomer form, and little to none greatly over 64,000 which can be molecules large enough to cause compliment activitation in mammalian organisms. Developing such a polymerization method is therefore very desirable in order to successfully find an oxygen transport substitute.

SUMMARY OF THE INVENTION

In one aspect the subject invention is a stable, cross-linked hemoglobin composition capable of transporting and releasing oxygen in living cells. The hemoglobin is essentially free of impurities and is cross-linked with an imidoester whereby the hemoglobin is present in predominantly tetramer and larger forms. The preferred imidoesters for cross-linking the hemoglobin are dimethyl adipimidate or dimethyl suberimidate. Hemoglobin predominantly in tetramer or larger form can be interpreted as where at least 80% of the cross-linked hemoglobin has a molecular weight of at least 64,000 Daltons, more preferably where at least 90 to 95% of the cross-linked hemoglobin has a molecular weight of at least 64,000 Daltons. In addition, the imidoester cross-linked hemoglobin is very stable to methemoglobin as compared to conventional means of cross-linking and has an oxygen affinity, p50, of at least 13 mm Hg.

The cross-linked hemoglobin composition can also include a pharmaceutically acceptable carrier medium for facilitating transfusion or injection into a mammal being treated or for use as an oxygen carrying fluid for analytic, transplant or laboratory usage. Typical pharmaceutically acceptable carrier medium can include purified water or saline solution.

In another aspect the subject invention is a method for preparing a cross-linked hemoglobin composition comprising a) collecting mammalian blood, b) separating red blood cells from the collected blood and washing the red blood cells, c) lysing the washed red blood cells, d) centrifuging the lysed blood cells to obtain a lysate of hemoglobin, e) purifying the lysate by anion or cation exchange chromatography, f) performing an ultrafiltration or microfiltration of eluted lysate obtained from the chromatography whereby purified hemoglobin is obtained, and g) cross-linking the purified hemoglobin with an imidoester to obtain a hemoglobin present in predominantly tetramer form.

The lysing of the red blood cells can be conducted by hypo-osmotic shock. The ultrafiltration is typically conducted with a 300,000 molecular weight membrane and the microfiltration is typically conducted with from about a 0.025 to about a 0.040 micron filter. Alternatively, cross-linking with imidoester step (g) can be performed after the lysate of hemoglobin is obtained in step (d) whereby step (e) begins with the purification of cross-linked hemoglobin. The method can additional include a step (h) where the purified, cross-linked hemoglobin is size excluded to remove low molecular weight hemoglobin (less than 64,000 Daltons). Typically, the size exclusion is by low pressure size exclusion chromatography.

The present invention therefore describes an imidoester, cross-linked hemoglobin composition essentially free of any impurities and being present in predominantly a tetramer or larger form which has improved stability to oxidation of the hemoglobin over more traditional forms of cross-linking hemoglobin such as with glutaraldehyde. The hemoglobin composition has a predominant molecular weight of at least 64,000 Daltons and has improved cross-link stability. The hemoglobin is suitable for use as a blood oxygen transport substitute for mammals or generally as an oxygen transport fluid.

DETAILED DESCRIPTION OF THE INVENTION

The present invention describes a method for purifying and cross-linking hemoglobin with certain imidoesters which have not been used to cross-link hemoglobin for use as a transfusion therapeutic. These bifunctional imidoester cross-linkers include dimethyl adipimidate and dimethyl suberimidate, among others. There are advantages in using these cross-linking agents over hemoglobin cross-linkers which have been used in the past. Particular reaction conditions have been discovered which provide a narrow molecular weight distribution and suitable transporting of oxygen.

Imidoesters such as dimethyl adipimidate and dimethyl suberimidate are bifunctional cross-linking reagents that react specifically and quickly with proteins under mild conditions. Stable, amidine adducts are formed with epsilon-amino groups of lysine residues and the amino terminal amine of polypeptide chains (Wold, F. (1972) Bifunctional reagents. Methods in Enz. 25: 623–651; Peters, K., and F. M. Richards (1977) Chemical cross-linking reagents and problems in studies of membrane structure. Ann. Rev. Biochem. 46: 523–551. The cross-linking reagent typically reacts with one-to-two amino groups per hemoglobin subunit. Some cross-linking occurs between the two beta chain lysine residues (beta-82) that stabilize the tetrameric form of human hemoglobin. Dimethyl adipimidate has been studied as an antisickling agent for hemoglobin S (Lubin, B. H., Pena, V., Mentzer, W. C., Bymun, E., Bradley, T. B., and L. Packer (1975) Dimethyl adipimidate: a new antisickling agent. Proc. Natl. Acad. Sci. U.S.A. 72: 43–46). Modification of the beta-82 lysines alters the conformation of the deoxygenated form of HbS and so prevents its crystallization or gelation. Crystallization is the molecular basis for tile sickling phenomenon seen with the afflicted red cells. Although modification of the beta-82 lysine by the cross-linking agent is required to prevent sickling, tile actual cross-linking of the two beta-82 lysines within a hemoglobin tetramer is not. The present invention uses the dimethyl adipimidate to bovine hemoglobin with the intent of forming both stabilized tetramers, caused by introducing intersubunit cross-links between the beta-82 lysines, and high molecular weight aggregates of stabilized tetramers, caused by introducing intermolecular cross-links between epsilon-amino groups of separate, stabilized, hemoglobin tetramers.

The advantages for cross-linking hemoglobin with imidoesters, and specifically dimethyl adipimidate is twofold: first, cross-linking will retard the dissociation of tetrameric hemoglobin of molecular weight 64,000, into 32,000 molecular weight dimers. In unmodified hemoglobin tetrameric and dimeric species are in a dynamic equilibrium. Stabilization of the tetrameric hemoglobin by cross-linking with imidoesters will substantially reduce the passage of hemoglobin into the renal tubules by preventing filtration across the membrane of the glomerular capsule.

Secondly, cross-linking will result in the formation of high molecular weight oligomers of the hemoglobin tetramer which would be extremely resistant to renal filtration and more stable to oxidation at physiological temperature than either unmodified hemoglobin or hemoglobin modified with the cross-linking agent glutaraldehyde.

Dimethyl adipimidate is a relatively inexpensive reagent and is available in bulk quantities. The cross-linking process utilizing dimethyl adipimidate lends itself well to scale up.

The oxygen binding properties of the various forms of bovine hemoglobin were measured and appear in Table I. The P50 is the partial pressure of oxygen at which 50% of the available sites have bound oxygen. The Hill coefficient or n value is an expression of the cooperativity among the oxygen binding sites with high n values denoting high cooperativity. The P50 values were measured during both the oxygenation and deoxygenation of the hemoglobin solution. The mean P50 values were: 13.5 mM Hg for dimethyladipimidate cross-linked hemoglobin, 14.25 mM Hg for the glutaraldehyde cross-linked hemoglobin and 23.75 mM Hg for unmodified bovine hemoglobin. If extreme cross-linking was carried out with imidoesters or glutaraldehyde, the p50 values for these hemoglobins was greatly decreased. Also, with both file imidoesters and glutaraldehyde, cross-linking of the hemoglobin reduced its cooperativity with the greater reduction being seen in the glutaraldehyde treated sample.

TABLE I

| Hb Sample | P50 Oxy | P50 Deoxy | n |
|---|---|---|---|
| Bovine Hb | 24.00 | 23.75 | 2.1-2.4 |
| Glutaraldehyde Cross-linked | 15.00 | 13.50 | 1.2 |
| DMA Cross-linked | 14.00 | 14.25 | 1.6 |
| Excess Glutaraldehyde | 7.00 | 6.50 | 1.1 |
| Excess DMA | 10.00 | 9.0 | 1.5 |

The stability of the various cross-linked hemoglobins was compared and showed the imidoester version to have superior stability. Therefore, the imidoester under proper cross-linking procedures, described below, yielded a better oxygen transport hemoglobin when considering stability and oxygen affinity.

In the 36°-37° C. incubation, the dimethyladipimidate cross-linked, glutaraldehyde cross-linked, and unmodified hemoglobin samples contained 2.5%, 8.0% and 3.5% methemoglobin, respectively, at file start of the incubation. After 5 hours at 36°-37° C. the percentages of methemoglobin were 8.9%, 44.4%, and 8% for the dimethyladipimidate cross-linked, glutaraldehyde cross-linked, and unmodified bovine hemoglobin samples, respectively. After 24 hours, the methemoglobin concentrations were 24.1, 87.9, and 42% for the dimethyladipimidate cross-linked, glutaraldehyde cross-linked, and unmodified bovine hemoglobin samples, respectively. After 48 hours the methemoglobin concentrations in dimethyladipimidate cross-linked and uncross-linked bovine hemoglobin samples were 46.5% and 68%, respectively. The dimethyladipimidate cross-linked hemoglobin was more stable than unmodified hemoglobin to methemoglobin formation. The literature reports that glutaraldehyde cross-linked human hemoglobin autooxidizes at a rate four times higher than unmodified human hemoglobin. Therefore, it was unexpected that the DMA cross-linked hemoglobin would be more stable than unmodified hemoglobin.

The stability of unmodified bovine hemoglobin and of dimethyladipimidate cross-linked and glutaraldehyde cross-linked bovine hemoglobin to autoxidation also was measured after incubation for 52 days at 4° C. in the same phosphate buffer as described above. After 28 days the dimethyladipimidate cross-linked bovine hemoglobin increased from 2.5% to 9.6% methemoglobin. Over the same time period the glutaraldehyde cross-linked hemoglobin increased from 8.0% to 23.5% methemoglobin. When measured after 52 days, the dimethyladipimidate cross-linked hemoglobin contained 14.3% methemoglobin while after 37 days the unmodified bovine hemoglobin contained 16.3% methemoglobin. As in the 37° C. incubation, the dimethyladipimidate cross-linked hemoglobin was significantly more stable than glutaraldehyde cross-linked hemoglobin or unmodified bovine hemoglobin.

In one aspect the invention relates to the enhancement of stability for mammalian hemoglobins including bovine hemoglobin, after cross-linking with imidoesters including dimethyl adipimidate. It is disclosed herein that the stability of mammalian hemoglobins can be enhanced by reaction with imidoesters, specifically dimethyl adipimidate under specific reaction conditions. In addition, a method for producing purified mammalian hemoglobin, specifically bovine hemoglobin is also disclosed. The hemoglobin would be essentially free of impurities which means that it would not contain any materials in a quantity which would cause any deleterious effects to the mammal treated. The hemoglobin would be sufficiently free of endotoxin (for example, less than 0.5 EU/ml at least a 40 mg/ml concentration of hemoglobin), phospholipid, viruses, and other nonhemoglobin proteins prior to cross-linking. However, it is also possible to first cross-link the hemoglobin after collection of the lysated hemoglobin and then purify the cross-linked hemoglobin, in fact, axis method may be more efficient for large scale production. The purified and cross-linked hemoglobin would be suitable as an oxygen transporting blood extender for transfusion into humans and animals.

Typically, the hemoglobin of the subject invention would be prepared by collecting the mammalian blood under aseptic conditions, washing the red cells, lysing the red cells, centrifuging the lysate, either ultrafiltrating with at least a 300,000 molecular weight membrane or microfiltrating with a 0.025 to about a 0.040 micron filter, purifying by anion or cation exchange chromatography to obtain a purified hemoglobin, then cross-linking with the imidoester and optionally performing a size exclusion chromatography or ultrafiltration to remove any low molecular weight hemoglobin. Alternatively, the hemoglobin may have been cross-linked after centrifuging and collecting the lysate. The purification steps could then be carried out including the optional size exclusion step.

The hemoglobin thus prepared would be essentially free of impurities and consist predominantly of a stabilized tetramer. Another way to characterize the cross-linked hemoglobin would be to state that it has a molecular weight distribution of predominantly at least 64,000. Predominantly or predominant as used herein means at least 80% of the cross-linked hemoglobin, preferably 90 to 95% of the cross-linked hemoglobin.

In order to prepare the subject specialized oxygen transport hemoglobin various cross-linking reaction parameters are specified. First, the concentration of chloride ion, and/or sodium chloride has a profound effect on the extent of cross-linking of (bovine) hemoglobin with DMA over the range of from 1 mM TRIS-HCl to 50 mM TRIS-HCl plus 2.0M NACl. In 1 and 10 mM TRIS-HCl, after 10 additions of DMA, 90.3% and 72.2% (respectively) of the hemoglobin remained unpolymerized. In contrast to this result, in the presence of 50 mM TRIS-HCl plus 0.5, 1.0, and 2.0M NACl, only 25.8, 24.4, and 20.7% remained uncross-linked (respectively). A steady decrease in the unpolymerized hemoglobin, and an increase in the high molecular weight (>400,000 daltons) was observed as the salt concentration was increased. The highest percentage of hemoglobin in the 64–400,000 range was observed when the cross-linking was done either in 50 mM TRIS-HCl or in 50 mM TRIS-HCl plus 100 mM NaCl.

Secondly, buffer type was shown to have a strong influence on cross-linking. For example, the DMA cross-linking reaction proceeded poorly in glycine-HCl, ethanolamine-HCl, and in a solution containing sodium phosphate plus lysine. In these buffer types, it is assumed that the primary amino function inhibited the cross-linking reaction, which is thought to occur primarily to amino groups on the N-terminus of the protein and its lysine residues. The greatest amount of cross-linking was seen in the presence of 2-amino-2-methyl-1-propanol buffer with only 23.4% of the hemoglobin remaining uncross-linked. This buffer, obviously, also has a primary amino functionality. The next four buffers in terms of DMA cross-linking efficiency were TRIS (Tris[hydroxymethyl]aminomethane), sodium carbonate, CHES (2-[N-Cyclohexylamino]ethanesulfonic acid), and CAPSO (3-[Cyclohexyl-amino]-2-hydroxy-1-propanesulfonic acid); three of which have primary amino functionalities. In contrast, CAPS (3-[Cyclohexylamino]-1-propanesulfonic acid) was not a good buffer for the cross-linking reaction, and the resulting product was only 27.2% cross-linked. Sodium phosphate also was not a good choice for the cross-linking reaction.

Thirdly, pH played an important role in effectively polymerizing hemoglobin in an imidoester. For example, attemps to cross-link hemoglobin with DMA at pH values lower than 8.0 were generally unsuccessful. At pH 8.0 after 10 additions of DMA and a final stoichiometric ratio of DMA to hemoglobin equal to 10, the hemoglobin was only 12.2% cross-linked. An increase in the cross-linking efficiency was witnessed at pH 9.0, 10.0, and 10.5, with only 58%, 48%, and 50%, respectively, remaining uncross-linked at the end of the DMA additions. It was apparent from the data, however, that the reaction of DMA with hemoglobin requires a pH of 9 or greater in order to be successful.

Finally, it was observed that deoxygenated hemoglobin was more readily cross-linked than oxygenated hemoglobin. After providing the above described polymerization conditions for optimum cross-linking, the uncross-linked hemoglobin can be filtered or chromatographed out to yield the 64,000 or greater molecular weight and then further filtering or chromatograph to yield predominantly 64,000 weight. Therefore, optimizing the cross-linking of the hemoglobin greatly facilitates the economical and practical preparation of the subject oxygen transfer material which is predominantly 64,000 to 300,000 molecular weight.

After the cross-linked hemoglobin is prepared it is typically placed in a pharmaceutically acceptable carrier medium appropriate for injecting or infusion into a mammal being treated. Typical pharmaceutically acceptable carrier medium can include physiologically acceptable salt solutions appropriate for injection or infusion such as saline solutions which are commercially available. A pharmaceutical acceptable carrier would be any of a variety of liquids which would be relatively inert to file cross-linked hemoglobin and would not have deleterious effect on the mammal being infused or injected. Suitable fluids can also include other blood products either natural or synthetic or fluorocarbon fluids. Generally the subject cross-linked hemoglobin would be admixed in a suitable pharmaceutical carrier whereby the hemoglobin concentration could be administered in adequate amount of from about 40 to about 140 mg/ml.

The subject invention is described in greater detail as follows for each of the various steps and molecular composition described above. The methods described apply to any mammalian hemoglobin even though for purposes of demonstration the specific examples which describe the purification, cross-linking and modification use bovine hemoglobin. Bovine hemoglobin does, however, have an advantage for having a very high p50 value suitable for oxygen transport.

EXAMPLE 1

Collection of Blood and Preparation of Red Cell Hemolysate

Blood was drawn in an aseptic manner from Holstein steers at the farm belonging to The Upjohn Company Agricultural Division. First, the hair was shaved from the neck of each steer with electrical clippers. The shaved area then was wiped with a cloth towel soaked in an iodine solution, followed by washing with 95% ethanol from a squirt bottle. The ethanol was allowed to air dry prior to blood drawing. The blood was drawn into 0.5–1.0 liter evacuated blood collection bottles which were sterile and pyrogen free. An appropriate amount of a sterile sodium heparin solution was added to each bottle prior to blood collection. The bottles were placed on ice immediately after filling, and were transported to the laboratory on ice. For initial studies, 2.5–5.0 liters of blood were drawn.

In the laboratory, all procedures were conducted either on ice or at 4° C. to minimize the growth of microorganisms and file concomitant pyrogen formation. In addition, the purification steps should be conducted in a clean environment with filtered air that has a low particulate content. The first steps in the purification of file hemoglobin involve the separation of the red blood cells from the blood plasma, followed by repeated washings of the red cells with a salt solution, and centrifugation to pellet the red cells. The whole blood first was transferred to pyrogen-free 0.5 liter centrifuge bottles and centrifuged for 30–40 minutes at 4000 RPM and 4° C. The red cells were pelleted during the centrifugation. The blood plasma in the supernatant was removed by aspiration. The red blood cells or erythrocytes were resuspended in an ice cold solution containing 16 grams of sodium chloride (NaCl) per liter of purified water. This solution is referred to as 1.6% saline. The red cells were resuspended by stirring with a sterile and pyrogen-free glass rod, or by gentle repeated inversion of the centrifuge bottle. After the red cells were resuspended, they were recentrifuged at 10,000 RPM for 30–40 minutes at 4° C. The red cells were resuspended in 1.6% saline and centrifuged again at 10,000 RPM for 30–40 minutes at 4° C. The red cells were washed with 1.6% saline a total of three times prior to red cell rapture or lysing.

After washing the cells, file red cells were lysed by hypo-osmotic shock in the following manner. To one volume of washed, pelleted red cells were added four volumes of ice cold 0.0025M sodium phosphate buffer, pH 7.4. The red cells were suspended in this dilute phosphate buffer by gentle inversion of the centrifuge bottles. After the cells were completely suspended, the red cell suspensions were incubated at 0°–4° C, for one hour, followed by centrifugation at 10,000 RPM for 30–90 minutes at 4° C. After centrifugation, the hemoglobin in the supernatant was recovered by aspiration. In certain experiments, the protocol was modified in the following manner. After the one hour incubation with 0.0025M sodium phosphate buffer at 0°–4° C., a 2.0M solution of sodium chloride was added to a final concentration of 0.2M prior to centrifugation. Addition of the sodium chloride to the red cell lysate provided a clearer supernatant after centrifugation.

A polishing step may be included after the centrifugation to produce the hemolysate. A filter aid which is either a cellulosic, dialomaceous earth, polymer, or silica derivative would be added to the centrifuged hemolysate with agitation. The filler aid would then be removed by filtration or centrifugation. Addition of a polishing step with a filter aid would remove additional stroma fragments, thus phospholipid, which would not be entirely removed by centrifugation.

An alternative to hypo-osmotic shock for lysing the red cells is mechanical disruption such as with a French press or a larger scale cell homogenizer.

The pyrogen content of the four hemolysates processed varied from 0.05 to 0.2 endotoxin units (EU) per ml by the Limulus Amoebocyte Lysate (LAL) pyrogen test. Downstream processing by anion exchange or cation exchange chromatography would remove the last traces of endotoxin and phospholipid.

EXAMPLE 2

Reduction of Virus Content

If the bovine blood is contaminated with viruses, a certain amount of viral load would be removed during washing of the red cells with low speed centrifugation. Another percentage would be removed with the high speed centrifugation of the hemolysate, and would reside in the pellet. Another aliquot would be removed in a polishing step.

Further reduction of vital load would be by microfiltration and/or ultrafiltration. Microfiltration with a 0.025–0.040 micron filter will greatly reduce the titer of most viruses. An Ultipor N66 nylon 66 microfiltration cartridge from Pall Corporation has a 0.04 micron porosity, and would be used to filter tile hemolysate prior to further downstream processing. In addition, if needed, a 300,000 molecular weight cutoff ultrafiltration membrane from Filtron Corporation is available which inserts into a Pellicon production scale ultrafiltration unit from Amicon Corporation. The hemoglobin would pass freely through all of these ultra- and microfiltration membranes, whereas a proportion of the viruses would be retained. Therefore, a combination of these two filtration membranes would greatly reduce the vital load. Each of these filter types shows low protein retention.

In addition to filtration, the viral content of the hemolysate or filtered hemolysate could be reduced by the addition of appropriate detergents, ethylenedinitrilotetraacetic acid, the FDA-approved reagent trinitrobutyl phosphate, or a combination of these additives.

EXAMPLE 3

Ion Exchange Chromatography of Hemoglobin

Anion exchange chromatography has been utilized extensively in the purification of mammalian hemoglobins (Williams, R. C., K. Tsay (1973) Anal. Biochem. 54:137–45). Under the proper pH and ionic strength conditions, hemoglobin can be applied to an anion exchanger so that it binds to the exchanger. Proteinaceous and non-proteinaceous impurities would be removed from hemoglobin during development of the column. Conditions also can be selected under which hemoglobin has little or no affinity for the selected ration exchange resin. Under these conditions, the impurities would be left behind on the column. The principle contaminants present in freshly prepared hemolysate are phospholipids, potentially residual virus which was not removed by upstream processing steps, low levels of bacterial endotoxin, and proteins other than hemoglobin. Endotoxin, phospholipid, and plasma proteins are more negatively charged than hemoglobin and should exhibit a higher affinity for the anion exchanger under the conditions selected. Under the proper loading and eluting conditions, anion exchange chromatography should be useful for resolving hemoglobin from these contaminants. In addition, anion exchange chromatography should further reduce the viral load.

We have utilized three anion exchange chromatographic protocols for the purification of hemoglobin: binding at elevated pH and elution with a descending pH gradient, binding at elevated pH and elution with a step gradient of lower pH, and loading under pH conditions in which the hemoglobin does not bind to the anion exchanger, but passes through the column unretained. All of our experiments have been carried out in a column mode, but it would be expected that similar batch conditions could be developed that would give nearly identical results. The anion exchanger utilized in these experiments was Q-SEPHAROSE Fast Flow from Pharmacia, but it would be expected that these procedures would work with a number of commercially available low to mid-pressure anion exchangers that have been developed for protein purification including those with quaternary amine and diethylaminoethyl functionalities.

Cation exchange chromatography also has been utilized extensively for the purification of mammalian hemoglobins (Bucci, E. (1981) Preparation of isolated chains of human hemoglobin, Meth. in Enzymol. 76: 97–106). Under the proper pH and ionic strength conditions, hemoglobin can be applied to a cation exchanger so that it binds to the exchanger. Phospholipid and endotoxin, as well as plasma proteins should have little affinity for the cation exchanger under conditions with which hemoglobin would bind. Under the proper loading and elution conditions, cation exchange chromatography should be useful for resolving hemoglobin from these contaminants. In addition, cation exchange chromatography would give an additional reduction in viral load.

Two cation exchange chromatographic protocols were designed for the purification of hemoglobin. In the first protocol, the hemoglobin was loaded under conditions in which it bound to the cation exchanger and was then eluted with a linear pH gradient. In the second protocol, the hemoglobin was loaded under conditions in which it binds to the resin, and then eluted with a step pH gradient. In both of these protocols the phospholipid and endotoxin would pass unretarded through the resin, thus resolving these contaminants from the hemoglobin. A number of commercially available cation exchangers would be adequate. Preferably, a S-SEPHAROSE Fast Flow from Pharmacia was used for its excellent protein binding and flow characteristics. A host of other low-to-mid-pressure chromatographic media with an Sulfopropyl- or Carboxymethyl- functionality would be expected also to perform the needed function. Scaling of these resins is economical.

EXAMPLE 3A

Anion Exchange Chromatography With a Linear pH Gradient

This experiment provided a demonstration of anion exchange chromatography conditions in which bovine hemoglobin was loaded onto the exchanger and then eluted with a linear pH gradient. A 2.5×5.5 cm column of Q-SEPHAROSE Fast Flow was prepared and cleaned by overnight exposure to 0.5M NaOH. The column was washed with 100 mM TRIS, pH 8.5 until the pH of the column effluent was 8.5. The column then was equilibrated with 50 mM TRIS, pH 8.5. Five ml of a sample of freshly prepared bovine red cell hemolysate containing approximately 350 mg of hemoglobin were diluted to 10 ml with 100 mM TRIS, pH 8.5 and loaded onto the Q-SEPHAROSE column at 2.5 ml per minute. Following loading, the column was washed with 50 mM TRIS, pH 8.5 until the absorbance of the column effluent returned to baseline. The column then was eluted with a linear gradient consisting of the starting buffer versus 50 mM TRIS, pH 6.5 over ten column volumes. The hemoglobin eluted essentially as a single major peak with several minor peaks eluting before and after it. The single major peak accounted for 95% of the hemoglobin which was loaded onto the column. All of the chromatographic procedures were carried out at 5° C.

EXAMPLE 3B

Anion Exchange Chromatography With a Step pH Gradient

This experiment provided a demonstration of anion exchange chromatography conditions in which bovine hemoglobin was loaded onto the exchanger and then eluted with a single pH step gradient. A 2.5×5.5 cm column of Q-SEPHAROSE Fast Flow was prepared and cleaned as in Example 3A. Eight ml of a sample of bovine red cell hemolysate containing approximately 400 mg of hemoglobin were diluted to 16 ml with 50 mM TRIS, pH 8.5 and loaded onto the column at 2.7 ml per min. Following loading the column was washed with 50 mM TRIS, pH 8.5 until the absorbance of the effluent returned to baseline. The column then was developed with 50 mM TRIS, pH 7.4 mid the hemoglobin eluted from the column essentially as a single peak. The mount of hemoglobin present in the Q-SEPHAROSE rich fraction was nearly identical to that loaded onto the column, indicating a nearly quantitative recovery across this step.

EXAMPLE 3C

Anion Exchange Chromatography In Which The Hemoglobin Is Not Retained

This experiment was a demonstration of anion exchange chromatography conditions in which the bovine hemoglobin did not bind to the anion exchanger, but passed through the column un-retained. a 2.5×5.5 cm column of Q-SEPHAROSE Fast Flow was prepared and cleaned by overnight exposure to 0.5 M NaOH. the column was washed with 100 mM TRIS, pH 7.4 until the pH of the column effluent measured 7.4. Ten ml of a freshly prepared bovine red cell hemolysate containing 880 mg of hemoglobin were diluted to 40 ml with 50 mM TRIS, pH 7.4, and 35 ml were loaded onto the column at 2.5 ml per min. Following loading, the column was washed with 50 mM TRIS, pH 7.4 until the hemoglobin had finished eluting from the column. The hemoglobin passed through the column without binding, and the recovery was 88%.

EXAMPLE 3D

Cation Exchange Chromatography of Hemoglobin

This experiment was a demonstration of cation exchange chromatography conditions in which bovine hemoglobin was loaded onto the exchanger and then eluted with a linear pH gradient. A 2.5×5.5 cm column of S-SEPHAROSE Fast Flow was prepared and cleaned by overnight exposure to 0.5M NaOH. The column was washed with 100 mM Bis-TRIS, pH 6.0 until the pH of the column effluent reached 6.0. The column then was equilibrated with 50 mM Bis-TRIS, pH 6.0. Five ml of a sample of freshly prepared bovine red cell hemolysate were diluted to 10 ml with 50 mM Bis-TRIS, pH 6.0 followed by loading onto the S-SEPHAROSE column at 2.5 minutes per hour. Following loading, the column was washed with 50 mM Bis-TRIS, pH 6.0 until tile absorbance of the column effluent reached baseline. The column then was eluted with a linear gradient between the column buffer and 50 mM Bis-TRIS, pH 8.0 over ten column volumes. All of the chromatographic procedures were conducted at 5° C.

EXAMPLE 4

Cross-Linking Bovine Hemoglobin With Dimethyl Adipimidate

A sample containing 170 mg/ml of purified bovine hemoglobin was treated as follows. The cross-linking reaction was carried out at a hemoglobin tetramer concentration of 1.75 mM, or 112 mg/ml. High tetramer concentrations promote the intermolecular cross-linking of hemoglobin tetramers. The hemoglobin is modified in file presence of 50 mM TRIS buffer, pH 8.8 at 4° C. The hemoglobin is modified by the addition of dimethyl adipimidate in equimolar amounts (i.e. 1.75 mM dimethyl adipimidate and 1.75 mM hemoglobin tetramer). The dimethyl adipimidate treatment is repeated eight times at 30 minute intervals at 4° C. For each application a 50 mg/ml solution of dimethyl adipimidate in 0.025M sodium carbonate, pH 9.25 is added to the hemoglobin solution to a final concentration of 1.75 mM. The hemoglobin solution is vortexed during addition of the cross-linker reagent, and then incubated on ice for 30 min. After 30 minutes a 0.4 ml sample was withdrawn and added to 4 ml of 0.25M sodium phosphate, pH 7.0. The phosphate buffer quenches the cross-linker reaction by hydrolysis of the imidoester. Quenching is carried out over two hours at room temperature. The remaining hemoglobin solution is again reacted with a fresh solution of the cross-linking agent. Eight cycles of reaction are carried out over 3.5 hours. In this experiment the specific imidoester dimethyl adipimidate was used. Other imidoesters could also be used.

EXAMPLE 5

Size Exclusion HPLC of Hemoglobin Cross-Linked With Dimethyl Adipimidate

Hemoglobin concentration was determined spectrophotometrically using published extinction coefficients (Benesch, R. E., Benesch R., S. Yung, (1973) Equations for the spectrophotometric analysis of hemoglobin mixtures. *Analyt. Biochem.* 55: 245–48). Reaction products were monitored after each addition of cross-linker using size exclusion HPLC (SEC-HPLC). Quenched reaction product was diluted to 1 mg hemoglobin tetramer per ml in 0.2M sodium phosphate, pH 7.0. The diluted product was analyzed by SEC-HPLC in two separate modes. The first was a Zorbax GF-250 SEC column (Dupont) equilibrated with 0.2M sodium phosphate, pH 7.0 and run at 1 ml/min. The second was a SUPEROSE 12 FPLC column (Pharmacia) equilibrated in 0.1M sodium phosphate, pH 7.0. Both columns had been calibrated with proteins of known molecular weight.

Successive iterations of cross-linking with dimethyl adipimidate resulted in a progressive increase in the amount of polymerized, tetramer stabilized, hemoglobin. The molecular weight ranges could be defined on SUPEROSE 12 SEC-HPLC as follows: 1) % <400,000 daltons, 2) %>64,000 daltons and <400,000 daltons, and 3) %<64,000 daltons. After four iterations of cross-linking the relative percent values were 1) 0%, 2) 40.64%, 3) 59.36%. After seven iterations the percent values were 1) 4.1%, 2) 50.4%, and 3) 45.5%. After eight iterations the percent values were 1) 7.5%, 2) 50.6%, and 3) 41.9%. The class 3 peak with a molecular weight value less than 64,000 daltons consisted of a single symmetrical peak with a molecular weight of 30,000 daltons. This fraction coeluted with unmodified bovine hemoglobin and is thought to consist mainly of hemoglobin dimer. The methemoglobin content of the hemoglobin after seven iterations of cross-linking was <2.5%. The visible spectrum of the cross-linked hemoglobin resembled that of unmodified bovine hemoglobin.

EXAMPLE 6

SDS Polyacrylamide Gel Electrophoresis of Cross-Linked Hemoglobin

Sodium dodecyl sulfate polyacrylamide gel electrophoresis (SDS-PAGE) was conducted on cross-linked and non-cross-linked hemoglobin samples as described. Hemoglobin samples were diluted to 2 mg/ml in 0.005M sodium phosphate, pH 7.4, 0.15 M NaCl, and the diluted samples were mixed with 3 paris of a standard SDS-gel buffer followed by incubation at 37° C. for 3 hours. Samples were run on 10–20% ISS mini-gels in the non-reduced form. SDS-PAGE of the cross-linked hemoglobin after 7 iterations of cross-linking indicated that 80% of the sample was cross-linked among subunits. At least eight multimers of the subunit molecular weight were present, all in approximately equal proportion.

EXAMPLE 7

Oxygen Equilibrium of Cross-Linked and Non-Cross-Linked Bovine Hemoglobin

An oxygen equilibrium measurement was determined for cross-linked and non-cross-linked bovine hemoglobin using a Hemoxanalyzer instrument from TCS Medical Industries. After seven iterations of reaction with dimethyl adipimidate a sample of cross-linked hemoglobin was diluted to 1.5 mg/ml in phosphate buffered saline, pH 7.4, and subjected to analysis. Also analyzed under identical conditions were a sample of unmodified bovine hemoglobin, and a sample of bovine hemoglobin which had been cross-linked in our laboratory with glutaraldehyde using methods as described (Guillochon, D. et at., (1986) Effect of glutaraldehyde on hemoglobin, *Biochem. Pharm.* 35: 317–23). The P50 values (oxygen partial pressure at half saturation) for the hemoglobin species were: 13.5 mm Hg for the dimethyl adipimidate cross-linked hemoglobin, 14.25 mm Hg for the glutaraldehyde cross-linked hemoglobin, and 23.75 mm Hg for unmodified bovine hemoglobin.

EXAMPLE 8

Stability Studies On Cross-Linked and Non-Cross-Linked Bovine Hemoglobin

Bovine hemoglobin which had been subjected to seven iterations of cross-linking with dimethyl adipimidate, unmodified bovine hemoglobin, and glutaraldehyde cross-linked hemoglobin were subjected to incubation at 36°-37° C. in 0.125M sodium phosphate, pH 7.1. The hemoglobin concentrations were 40 mg/ml for dimethyl adipimidate cross-linked bovine hemoglobin and unmodified bovine hemoglobin, and 28 mg/ml for glutaraldehyde cross-linked bovine hemoglobin. At certain time intervals samples of each hemoglobin species were removed, diluted 1/100 in 0.25M sodium phosphate buffer, pH 7.3 and scanned between 680 nm and 420 nm in a Shimadzu Model 160 UV-visible scanning spectrophotometer. Methemoglobin content was determined by analysis of each spectrum using published equations (Benesch, R. E. et al., (1973) Equations for the spectrophotometric analysis of hemoglobin mixtures, *Anal. Biochem.* 55: 245–48). Spectra were taken at 22° C.

Dimethyl adipimidate cross-linked bovine hemoglobin and glutaraldehyde cross-linked hemoglobin also were incubated at 4° C. over a more extended time period. Samples were taken at time intervals, and the methemoglobin content was determined as described above.

In the 36°-37° C. incubation, the dimethyl adipimidate cross-linked, glutaraldehyde cross-linked, and unmodified hemoglobin samples contained 2.5%, 8.0%, and 3.5% methemoglobin, respectively, at the start of the incubation. After 5 hours at 36°-37° C. the percentages of methemoglobin were 8.9%, 44.4%, and 8%, respectively, for the dimethyl adipimidate cross-linked, glutaraldehyde cross-linked, and unmodified bovine hemoglobin samples, respectively. After 24 hours, the methemoglobin concentrations were 24.1, 87.9, and 42% for the dimethyl adipimidate cross-linked, glutaraldehyde cross-linked, and unmodified bovine hemoglobin samples, respectively. After 48 hours the methemoglobin concentrations in dimethyl adipimidate cross-linked and uncross-linked bovine hemoglobin samples were 46.5% and 68%, respectively. The dimethyl adipimidate cross-linked hemoglobin is more stable to methemoglobin formation than unmodified bovine hemoglobin at 36°–37° C. The literature teaches that glutaraldehyde cross-linked human hemoglobin autoxidizes at a rate four times that of modified human hemoglobin (Guillochon, D. et al., (1986) Effect of glutaraldehyde on hemoglobin, *Biochem. Pharm.* 35: 317–23). It was unexpected that the dimethyl adipimidate cross-linked bovine hemoglobin would be more stable than unmodified bovine hemoglobin with respect to autoxidation.

The stability of dimethyl adipimidate cross-linked and glutaraldehyde cross-linked bovine hemoglobin to autoxidation also was measured after incubation for 28 days at 4° C. in the same phosphate buffer as described above. After 28 days the dimethyl adipimidate cross-linked bovine hemoglobin increased from 2.5% to 9.6% methemoglobin. Over the same time period the glutaraldehyde cross-linked hemoglobin increased front 8.0% to 23.5% methemoglobin.

EXAMPLE 9

Preparative Size Exclusion Chromatography of Dimethyl Adipimidate Cross-Linked Bovine Hemoglobin Preparative size exclusion chromatography was utilized to remove low molecular weight species, i.e. <64,000 daltons, from dimethyl adipimidate cross-linked bovine hemoglobin. Dimethyl adipimidate cross-linked hemoglobin, 40 mg/ml, was applied to a 2.5×90 cm column of Sephacryl S-200 HR (Pharmacia) equilibrated in 0.025M sodium phosphate, 0.15M NaCl, pH 7.4, at 4° C. The loading volume was 1% of the column bed volume, and the flow rate was 0.45 ml/min. Peaks from chromatography were pooled, and the pooled samples were analyzed by SEC-HPLC on a SUPEROSE 12 column (as described above) to determine the molecular weight distribution of hemoglobin species within them. The pre-column or load sample also was analyzed on the Superose 12 column.

Preparative size exclusion chromatography separated the DMA cross-linked hemoglobin into two major fractions. Fraction 1 contained the higher molecular weight cross-linked hemoglobin species, and represented 51.3% of the total recovered hemoglobin. Fraction 2 contained cross-linked hemoglobin of molecular weight less than 64,000. SEC-HPLC of the pre-column cross-linked hemoglobin fraction indicated it to contain 2.6% as >400,000 daltons, 47.2% >64,000 daltons, and 50.2% <64,000 daltons. From analytical SEC-HPLC, purified fraction 1 from preparative size exclusion chromatography contained 4.7% as >400,000 daltons, 92.7% as >64,000 daltons, and 2.6% as <64,000 daltons. This method was successful at removing the lower molecular weight hemoglobin species.

We claim:

1. A method for preparing a cross-linked hemoglobin composition for transporting oxygen to living cells, comprising cross-linking a purified hemoglobin lysate with dimethyl adipimidate or dimethyl suberimidate at a pH of at least 8.0, in a polymerization solution comprising TRIS-HCl buffer whereby at least 80% of said cross-linked hemoglobin has a molecular weight of 64,000 and a P50 of at least 13.

2. The method of claim 1 where said polymerization solution includes NaCl.

3. The method of claim 1 where said pH is from 8.0 to about 12.0.

4. The method of claim 1 where said polymerization solution contains 50 mM TRIS-HCl and from about 0.1 to about 2.0M NaCl.

5. The method of claim 1 where said purified hemoglobin lysate is deoxygenated.

6. The method of claim 1 which includes the removal of low molecular weight hemoglobin below 64,000 by size exclusion.

7. The method of claim 6 where said size exclusion is by chromatograph.

8. The method of claim 1 where said imidoester is dimethyl adipimidate.

9. The method of claim 1 wherein said polymerization is carried out by repeated treatments of said purified hemoglobin with equimolar amounts of dimethyl adipimidate or dimethyl suberimidate.

* * * * *